United States Patent [19]

Deinhammer et al.

[11] 4,046,792
[45] Sept. 6, 1977

[54] PROCESS FOR PREPARING METHYLTIN CHLORIDES

[75] Inventors: Wolfgang Deinhammer; Manfred Wick; Antonio Macri, all of Munich, Germany

[73] Assignee: Consortium fur Elektrochemische Industrie GmbH, Munich, Germany

[21] Appl. No.: 662,482

[22] Filed: Mar. 1, 1976

[30] Foreign Application Priority Data

Mar. 4, 1975 Germany .............................. 2514459

[51] Int. Cl.$^2$ ................................................ C07F 7/22
[52] U.S. Cl. ............................ 260/429.7; 260/448.2 P
[58] Field of Search ...................................... 260/429.7

[56] References Cited

U.S. PATENT DOCUMENTS

| | | | |
|---|---|---|---|
| 3,061,424 | 10/1962 | Nizsche et al. | 260/429.7 X |
| 3,541,126 | 11/1970 | Baronnier et al. | 260/429.7 X |
| 3,752,835 | 8/1973 | Shapiro et al. | 260/429.7 |
| 3,754,012 | 8/1973 | Bulten | 260/429.7 |

OTHER PUBLICATIONS

Poller, The Chemistry of Organotin Compounds, Academic Press, N.Y. pp. 58 and 66 (1970).
Chemical Abstracts V45, 5611i (1951).
Chemical Abstracts V42, 6742f (1948).

*Primary Examiner*—Helen M. S. Sneed

[57] ABSTRACT

A process for preparing methyltin chlorides which comprises reacting tetramethylsilane with tin tetrachloride.

5 Claims, No Drawings

PROCESS FOR PREPARING METHYLTIN CHLORIDES

The present invention relates to methyltin chlorides and more particularity to a process for preparing methyltin chlorides.

Heretofore methyltin chlorides (also referred to as methylchlorostannanes) have been prepared by direct synthesis from a copper-tin alloy ($Cu_3Sn$) and methyl chloride or by reacting tin tetrachloride with tetramethyltin ["Ullmanns Encycklopadie der Technischen Chemie", vol. 12, Munich-Berlin 1960, (Page 381)].

Compared to the processes known heretofore for the production of methyltin chlorides, the process of this invention provides several advantages. For example, it does not employ compounds, which are relatively difficult to obtain or compounds which are relatively difficult to handle. Moreover, it does not require catalysts which are difficult to acquire. Furthermore, the process of this invention can be carried out at lower temperatures and provides for a considerably better yield of desired product.

Therefore it is an object of this invention to provide a process for preparing methyltin chlorides. Another object of this invention is to provide a process for preparing methyltin chlorides at lower temperatures. Still another object of this invention is to provide a process for preparing methyltin chlorides which utilizes catalysts that are readily available. A further object of this invention is to provide a process for preparing methyltin chlorides with higher yields and at lower temperatures.

These and other objects which will become apparent from the following description are accomplished by reacting tetramethylsilane with tin tetrachloride in accordance with the following equation:

$$SnCl_4 + n(CH_3)_4Si \rightarrow (CH_3)_nSnCl_{4-n} + n(CH_3)_3SiCl.$$

in which $n$ represents 1, 2 or 3.

The tetramethylsilanes which are obtained as a by product from the reaction of silicon with methyl chloride to form methylchlorosilanes are utilized in the process of this invention.

Moreover, the trimethylchlorosilane by product obtained from the process of this invention is also a very desirable product and in contrast to the redistribution of organosilanes, the trimethylchlorosilane is essentially the only silane obtained. The trimethylchlorosilane can for example be used for treating organic compounds or inorganic compounds, such as silicon dioxide fillers, to render them hydrophobic. Furthermore, the trimethylchlorosilane by product can be employed in the conventional methods known in the art for endblocking organopolysiloxanes.

Although the temperature range for reacting tetramethylsilane with tin tetrachloride is not critical, it is preferred that the reaction be conducted at a temperature of from 20° to 250° C.

Also, it is preferred that the process be conducted in the presence of at least one catalyst which accelerates the exchange between the Si-linked methyl groups and the chloride. Suitable examples of such catalysts are $AlBr_3$, $AlCl_3$, $AlI_3$, $GaBr_2$, $GaCl_2$, $BCl_3$, $FeCl_3$; alkali halogen aluminates, such as sodium chloroaluminate and organoaluminum complexes, such as the sodium chloride complex of methylaluminum dichloride. Mixtures of various catalysts which accelerate the exchange of the Si-linked methyl groups with the chloride may also be employed.

Aluminum chloride is the preferred catalyst because it is readily available, highly effective and surprisingly selective. It is preferred that the aluminum chloride be used in amounts of from 0.1 to 15 percent by weight and more preferably in amounts of from 1 to 6 percent by weight, based on the weight of the tetramethylsilane employed.

When aluminum chloride is used as the catalyst in the process of this invention, the process is preferably carried out at a temperature of from 20° to 100° C and more preferably between 50° and 90° C. This results in exceptionally high yields, even in the absence of a small amount of a monomeric silane having at least one Si-linked hydrogen atom. However, the use of such a silane should not be excluded.

Although the mol ratio of tetramethylsilane to tin tetrachloride is not critical, it is preferred that from 1 to 15 mols of tetramethylsilane be employed for each mol of tin tetrachloride in the process of this invention. When it is desired to prepare a composition which contains dimethyltin dichloride containing only a small amount of methyltin trichloride, but which is free of trimethyltin chloride, then it is preferred that from 1.90 to 1.99 mols of tetramethylsilane be employed for each mol of tin tetrachloride.

However, when it is desired to prepare dimethyltin dichloride which is free of methyltin trichloride and trimethyltin chloride, then 2 mols of tetramethylsilane are employed for each mol of tin tetrachloride. It was found that even in the presence of aluminum chloride, that dimethyltin dichloride and trimethylchlorosilane are produced in essentially quantitative yields. This is especially surprising since U.S. Pat. No. 2,647,136 to Sauer, discloses that when dimethyldichlorosilane is heated in the presence of aluminum chloride, trimethylchlorosilane and methyltrichlorosilane are obtained and when trimethylchlorosilane is heated in the presence of aluminum chloride, dimethyldichlorosilane and tetramethylsilane are obtained.

When methyltin chloride is the desired product, then it is preferred that at least 4 mols of tetramethylsilane be employed for each mol of tin tetrachloride in the process of this invention.

The reaction can be conducted in the presence of organic solvents, if desired. Suitable solvents which may be employed are hydrocarbons having from 1 to 10 carbon atoms, such as for example, aliphatic or cycloaliphatic hydrocarbons.

Generally the tetramethylsilane employed in the process of this invention need not be separated from the hydrocarbons which are generated in the formation of the tetramethylsilane.

The process may be carried out at pressures ranging from atmospheric pressure up to superatmospheric pressure. It is preferred that the process be carried out at atmospheric pressure, i.e., at 760 mm Hg (abs) or at approximately 760 mm Hg (abs) and up to about 35 kg/cm².

In order to achieve good mixing of the reactants with the catalyst, it is preferred that the mixture be agitated.

Although the reaction time is not critical and may range from about 30 minutes up to 24 hours, it is preferred that the reaction time be from 1 to about 10 hours.

When the reaction is completed, the trimethylchlorosilane can be distilled off and the residue from the distillation can be recrystallized, sublimed or distilled. Also the distillation residue can be used in other reactions, for example, it can be reacted with a mercaptocarbonic acid ester, such as thioglycol acid isooctyl ester or with beta-mercaptopropionic acid isooctyl ester in the presence of water.

Various embodiments of the invention are further illustrated in the following examples in which all parts are by weight unless otherwise specified.

EXAMPLE 1

About 45 parts of a mixture containing 86 percent by weight of tetramethylsilane and 14 percent by weight of isopentane are added to a pressure vessel containing 57.2 parts of tin tetrachloride and 2.2 parts of aluminum chloride and heated to 80° C with constant agitation over a period of 5 hours. The contents of the reaction vessel are distilled off and after removing the other components having a lower boiling point, about 43.3 parts of trimethylchlorosilane are obtained in the distillate. About 51.5 parts of the distillation residue are recovered and according to the NMR spectrum, contain about 93 percent by weight of dimethyltin dichloride and about 2 percent by weight of trimethylchlorosilane. The yield of dimethyltin dichloride is about 99 percent of theoretical, based on the tin tetrachloride employed. Sublimation of this product at 12 mm Hg (abs) produced 47.5 parts of pure dimethyltin dichloride.

EXAMPLE 2

About 45 parts of a mixture containing 86 percent by weight of tetramethylsilane and 14 percent by weight of isopentane are added to a pressure vessel containing 14.3 parts of tin tetrachloride and 2 parts of aluminum chloride and heated to 75° C for 3.5 hours with constant agitation. After cooling to room temperature, the contents of the reaction vessel formed two phases, one phase being crystalline and the other is a fluid above the crystalline phase. About 10.8 parts of the crystalline phase is obtained which according to the NMR spectrum contains 7.5 parts of trimethyltin chloride. About 50.1 parts of the fluid phase are recovered which contains 1.9 parts of trimethyltin chloride. The yield of trimethyltin chloride is about 86 percent of theoretical based on the tin tetrachloride employed.

Although specific examples of the invention have been described, it is not intended to limit the invention solely thereto, but to include all the variations and modifications falling within the spirit and scope of the appended claims.

What is claimed is:

1. A process for the preparation of methyltin chlorides, which comprises reacting tetramethylsilane with tin tetrachloride at a temperature of from about 20° to 250° C.

2. The process of claim 1, wherein the reaction is carried out in the presence of a catalyst which promotes the exchange of methyl and chloride groups.

3. The process of claim 2 wherein the catalyst is aluminum chloride.

4. The process of claim 1 wherein from 1.9 to 1.99 mols of tetramethylsilane is used for each mol of tin tetrachloride.

5. The process of claim 1 wherein 2 mols of tetramethylsilane are used for each mole of tin tetrachloride.

* * * * *